United States Patent
Nakamura et al.

(10) Patent No.: US 11,890,174 B2
(45) Date of Patent: Feb. 6, 2024

(54) STRETCHABLE SHEET, WORN ARTICLE USING THE SAME, AND STRETCHABLE SHEET MANUFACTURING APPARATUS

(71) Applicant: ZUIKO CORPORATION, Osaka (JP)

(72) Inventors: Hideyuki Nakamura, Osaka (JP); Miwa Koshijima, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 652 days.

(21) Appl. No.: 16/330,082

(22) PCT Filed: Sep. 11, 2017

(86) PCT No.: PCT/JP2017/032634
§ 371 (c)(1),
(2) Date: Mar. 2, 2019

(87) PCT Pub. No.: WO2018/070158
PCT Pub. Date: Apr. 19, 2018

(65) Prior Publication Data
US 2019/0209396 A1     Jul. 11, 2019

(30) Foreign Application Priority Data
Oct. 14, 2016   (JP) ................. 2016-202382

(51) Int. Cl.
*A61F 13/49*          (2006.01)
*A61F 13/15*          (2006.01)

(52) U.S. Cl.
CPC .. *A61F 13/49012* (2013.01); *A61F 13/15593* (2013.01); *A61F 13/15764* (2013.01);
(Continued)

(58) Field of Classification Search
CPC .......... A61F 13/49012; A61F 13/15593; A61F 13/15764; A61F 2013/15869
See application file for complete search history.

(56) References Cited

U.S. PATENT DOCUMENTS 5,626,944 A * 5/1997 Rasmussen ........... B29C 55/085
428/172
10,758,428 B2 * 9/2020 Nakamura ............ A61F 13/49
(Continued)

FOREIGN PATENT DOCUMENTS

JP       2008-154998 A      7/2008
JP       2009-034209 A      2/2009
(Continued)

OTHER PUBLICATIONS

International Search Report Issued in PCT/JP2017/032634 dated Dec. 12, 2017.

*Primary Examiner* — Tong Guo
(74) *Attorney, Agent, or Firm* — Renner, Otto, Boisselle & Sklar, LLP (57) ABSTRACT

A stretchable sheet 10 includes: a plurality of attached portions 3 spaced apart from each other in the direction of stretch Df, wherein the first surfaces 1f and 2f of a pair of sheets 1 and 2 are attached to each other by being welded without using an adhesive, at the attached portions 3, the attached portions 3 hold elastic members F, and the attached portions 3 extend in a direction Dp crossing the direction of stretch Df of the elastic members F; and a plurality of folds P that appear between the attached portions 3 while the elastic members F are shrunk, wherein the attached portions 3 include: a plurality of strongly-attached portions 3s arranged on opposite sides of each elastic member F in the crossing direction Dp; and a plurality of weakly-attached portions 3w arranged between adjacent elastic members F and between adjacent strongly-attached portions 3s.

9 Claims, 10 Drawing Sheets

(52) U.S. Cl.
CPC .... *A61F 13/4902* (2013.01); *A61F 13/49011* (2013.01); *A61F 2013/15869* (2013.01); *A61F 2013/49025* (2013.01)

(56) References Cited

U.S. PATENT DOCUMENTS

| | | | | |
|---|---|---|---|---|
| 2003/0096548 A1* | 5/2003 | Groitzsch | ............... | B32B 5/026 |
| | | | | 442/268 |
| 2003/0144643 A1* | 7/2003 | Jarpenberg | ........ | A61F 13/15593 |
| | | | | 604/385.24 |
| 2004/0116884 A1* | 6/2004 | Fujii | ..................... | A61F 13/536 |
| | | | | 604/367 |
| 2009/0275909 A1 | 11/2009 | Sakaguchi | | |
| 2011/0045231 A1* | 2/2011 | Kajiwara | .................. | B32B 5/26 |
| | | | | 428/91 |
| 2011/0123773 A1* | 5/2011 | Lofink | ..................... | B31F 1/07 |
| | | | | 428/166 |

FOREIGN PATENT DOCUMENTS

| | | | |
|---|---|---|---|
| JP | 2009-118986 A | | 6/2009 |
| JP | 2009-153913 A | | 7/2009 |
| JP | 2012-126140 A | | 7/2012 |
| JP | 2014-198180 | * | 10/2014 |
| JP | 2014-198180 A | | 10/2014 |
| JP | 2015-058226 A | | 3/2015 |
| JP | 2015-104606 A | | 6/2015 |
| JP | 2015-192862 A | | 11/2015 |

\* cited by examiner

FIG. 10C

STRETCHABLE SHEET, WORN ARTICLE USING THE SAME, AND STRETCHABLE SHEET MANUFACTURING APPARATUS

TECHNICAL FIELD

The present invention relates to a stretchable sheet, a worn article using the same, and a stretchable sheet manufacturing apparatus.

BACKGROUND ART

A structure in which a plurality of elastic members are sandwiched between two sheets, wherein the two sheets are welded together and elastic members are secured between the two sheets at attached portions that extend in a direction crossing the direction of stretch of the elastic members, is known in the art as a structure of a stretchable sheet (first patent document).

CITATION LIST

Patent Literature

[First Patent Document] JP2014-198180A (front page)

SUMMARY OF INVENTION

With such a stretchable sheet as described above, the sheets are secured together and the sheet and the elastic members are secured together at the attached portions. Therefore, at least portions of the sheets at the attached portions are heated and melted. Melted positions more easily tear than un-melted positions. The attached portions that easily tear are normally extending long continuously or intermittently in order to clearly form folds between adjacent attached portions, and the sheets may possibly break along the long attached portions.

Thus, it is an object of the present invention to provide a stretchable sheet, a worn article and a stretchable sheet manufacturing apparatus, wherein the elastic members are firmly secured to the sheets, and the attached portions do not easily tear.

A stretchable sheet of the present invention includes:
a pair of sheets 1 and 2, wherein a first surface 1*f* of one of the pair of sheets and a first surface 2*f* of another one of the pair of sheets oppose (face) each other or are in contact with each other;
a plurality of elastic members F that are arranged between the first surfaces 1*f* and 2*f* of the pair of sheets 1 and 2 and are arranged spaced apart from each other;
a plurality of attached portions 3, wherein the first surfaces 1*f* and 2*f* of the pair of sheets 1 and 2 are attached to each other by a welding construction (a welded structure) without using an adhesive, at the attached portions 3; the attached portions 3 hold the elastic members F; the attached portions 3 extend in a direction Dp crossing a direction of stretch Df of the elastic members F; and the attached portions 3 are spaced apart from each other in the direction of stretch Df between adjacent elastic members F of the elastic members F; and
a plurality of folds (pleats) P that appear between the attached portions 3 in a state where the elastic members F are shrunk,
wherein the attached portions 3 include:

a plurality of strongly-attached portions 3*s* arranged on opposite sides of each of the elastic members F in the direction Dp crossing the direction of stretch Df of the elastic members F; and
a plurality of weakly-attached portions 3*w*; each of the weakly-attached portions 3*w* being arranged between adjacent elastic members F of the elastic members F and between adjacent strongly-attached portions 3*s* of the strongly-attached portions 3*s*,
wherein a strength of attachment (a joint strength) between the pair of sheets 1 and 2 at the weakly-attached portions 3*w* is less than a strength of attachment (a joint strength) between the pair of sheets 1 and 2 at the strongly-attached portions 3*s*.

With the invention of the present sheet, the strongly-attached portions are arranged on the opposite sides of the elastic members, and the weakly-attached portions are arranged between the strongly-attached portions. The elastic members are secured to the sheets with a high reliability at the strongly-attached portions, and the sheets are prevented from melting at the weakly-attached portions, thereby preventing the lowering of the intrinsic tear strength of the sheets. This prevents the sheets from breaking along the attached portions.

At the weakly-attached portions, the sheets are prevented from melting. Thus, the stretchable sheet is soft.

Moreover, with the provision of the weakly-attached portions, it is possible to increase the surface pressure during a sealing process at the strongly-attached portions that are on the opposite sides of the positions where the elastic members are secured to the sheets, and it is possible to reliably secure the elastic members to the sheets.

Since the attached portions extend in the crossing direction Dp, the folds are likely to be formed clearly and continuously, thereby realizing a flexible stretchable sheet that has a good feel.

On the other hand, an apparatus for manufacturing the stretchable sheet of the present invention includes:
an anvil roll 50 for carrying the pair of sheets 1 and 2 and the elastic members F so that the elastic members F are arranged between the pair of sheets 1 and 2; and
a welding device 70, in cooperation with the anvil roll 50, for welding together the pair of sheets 1 and 2 so that the elastic members F are held by the pair of sheets, wherein:
the anvil roll 50 has a plurality of ridges 52 that are formed on a circumferential surface 51 of the anvil roll 50 and extend in a width direction S of the anvil roll 50;
each of the ridges 52 includes a plurality of high ridge portions 52H for producing the strongly-attached portions 3*s* and a plurality of low ridge portions 52L for producing the weakly-attached portions 3*w*;
the high ridge portions 52H and the low ridge portions 52L are provided intermittently in the width direction S; and
a height H1 of the low ridge portions 52L (each low ridge portion 52L) is lower than a height H2 of the high ridge portions 52H (each high ridge portion 52H).

With the invention of the present manufacturing apparatus, the pressure to be applied to the sheets at the low ridge portions is lower than at the high ridge portions. Therefore, at the low ridge portions, the pair of sheets are welded together while being soft. Therefore, it is easy to realize weakly-attached portions with a soft texture.

On the other hand, at the high ridge portions where the pressure is high, the pair of sheets are reliably welded together. Therefore, it is possible to stably hold the elastic members F at the strongly-attached portions.

In a worn article of the present invention using the stretchable sheet, the worn article has a skin-contact surface configured to be in contact with a skin of a wearer, and a non-skin-contact surface that is opposite thereto; and the folds P protrude on the skin-contact surface and/or the non-skin-contact surface.

Such a worn article will have a good texture and prevent stuffiness.

BRIEF DESCRIPTION OF DRAWINGS

In FIGS. 3(a), 3(c) and 3(d), non-woven fabric sheet positions are shown in gray. In FIG. 2A, weakly-attached portions are dotted and strongly-attached portions are hatched. In FIG. 5 and FIG. 6, the difference in height between high ridge portions and low ridge portions is not shown.

DESCRIPTION OF EMBODIMENTS

With a preferred stretchable sheet, a length Lw of the weakly-attached portions $3w$ (each weakly-attached portion $3w$) is greater than a length Ls of the strongly-attached portions $3s$ (each strongly-attached portion $3s$).

With an apparatus for manufacturing such a stretchable sheet, a length L1 of the low ridge portions 52L (each low ridge portion 52L) in the width direction S is longer than a length L2 of the high ridge portions 52H (each high ridge portion 52H) in the width direction S.

In such a case, long weakly-attached portions will enhance the advantageous effects of the present invention. On the other hand, even if the strongly-attached portions are short, the force by which the elastic members F are secured to the sheets is unlikely to lower.

With a preferred stretchable sheet, a thickness Tw of the weakly-attached portions $3w$ is greater than a thickness Ts of the strongly-attached portions $3s$. Note that with the thicknesses Ts and Tw, it is preferred to compare between the average thicknesses of these attached portions or between the thicknesses at the thinnest positions of these attached portions.

With a preferred manufacturing apparatus for obtaining such a stretchable sheet, a height H1 of the low ridge portions 52L is lower by 1 to 50 μm than a height H2 of the high ridge portions 52H.

In such a case, it is possible to realize flexible weakly-attached portions and to realize strongly-attached portions where the elastic members F are stably secured.

Depending on the thickness of the pair of sheets, the difference Δ between the height of the low ridge portions 52L and the height of the high ridge portions 52H (FIG. 8B) is more preferably 3 to 40 μm, and most preferably 5 to 30 μm. If the height difference Δ is too small, flexible weakly-attached portions are not realized, and if the difference Δ is too large, the sheets are less likely to be attached together at the weakly-attached portions.

With a preferred manufacturing apparatus, each of the ridges 52 of the anvil roll 50 includes a plurality of carrying grooves G that extend in a circumferential direction R of the anvil roll 50, and carry the elastic members F with the elastic members F being held in the carrying grooves G; and each of the carrying grooves G is defined by the high ridge portions 52H that are on opposite sides of each carrying groove G in the width direction S.

In this case, it is possible with the carrying grooves G to stably carry the elastic members F. The pair of sheets are secured to the elastic members F with the elastic members F being held in the carrying grooves G. Therefore, it is possible to prevent the contact pressure from being excessively at positions of the sheets that overlap with the elastic members F.

Preferably, the welding device is an ultrasonic welding device including an ultrasonic horn 71 that opposes the ridges 52 with the pair of sheets 1 and 2 and the elastic members F interposed therebetween, and to which an ultrasonic energy is given.

During an ultrasonic thermal bonding, the horn heats the sheets using the frictional heat caused by the contact with the sheets. Therefore, even if the contact pressure is small at the low ridge portions 52L, the reliability of the seal at the low ridge portions 52L will not be lowered.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiments

Prior to the description of embodiments of the stretchable sheet, an example structure of a disposable worn article using the stretchable sheet will be described.

Figure 1:
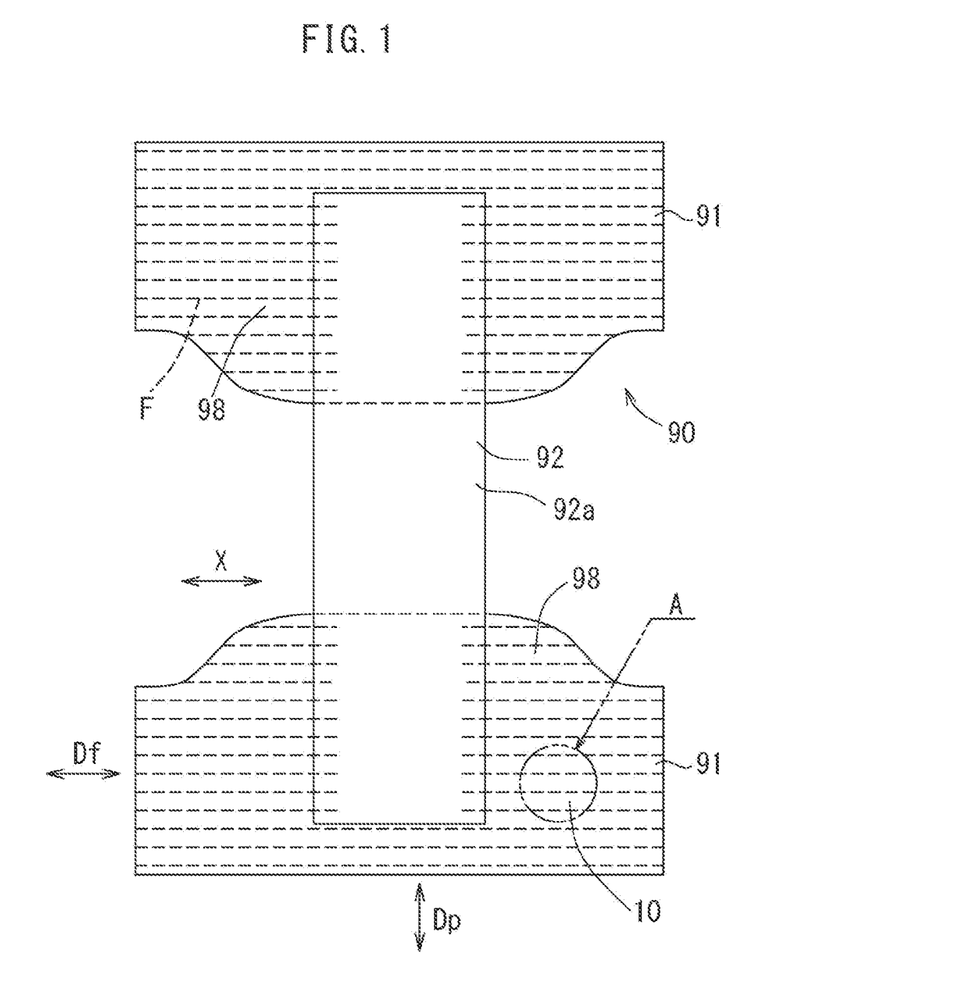
FIG. 1 is a plan view showing, flattened, an example of a worn article to which the present invention is applied.

FIG. 1 shows a worn article in a flattened state, wherein a worn article 90 includes an absorbent body 92 and a pair of, front and rear, around-torso members 91 and 91. The absorbent body 92 is provided so as to bridge between the pair of around-torso members 91 and 91, thereby forming a crotch portion 92a.

The present worn article 90 is worn while the crotch portion 92a is folded in two along a virtual line that is parallel to the girth direction X. Thus, the end portions of the pair of around-torso members 91 and 91 in the girth direction X overlap with each other.

Figure 2A:
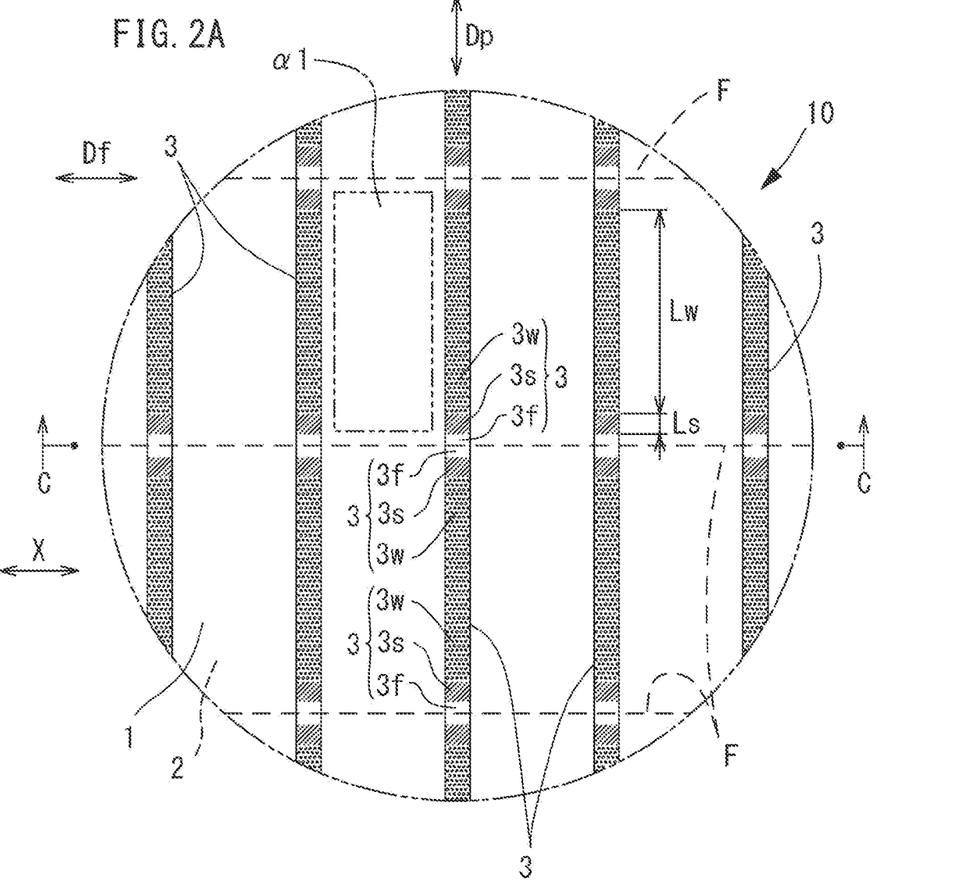
FIG. 2A is an enlarged plan view of the A part (stretchable sheet) according to Embodiment 1.
Figure 2B:
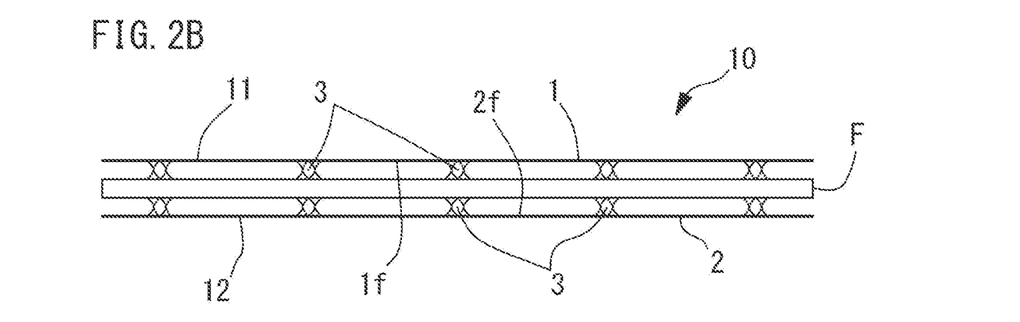
FIG. 2B is an enlarged cross-sectional view of the stretchable sheet of Embodiment 1.

The front and rear around-torso members 91 each include a stretchable sheet 10 clearly shown in FIG. 2A and FIG. 2B. The stretchable sheet 10 includes a laminate including elastic members F and the first sheet 1 and the second sheet 2 layered together.

The first sheet 1 and the second sheet 2 are each made of an air-permeable non-woven fabric. The elastic members F are sandwiched between the first sheet 1 and the second sheet 2, and are stretchable in the girth direction X.

The stretchable sheet 10 of the worn article 90 (FIG. 1) has a skin-contact surface 11 to be in contact with the skin of the wearer, and a non-skin-contact surface 12 on the opposite side.

Next, Embodiment 1 of the stretchable sheet 10 will be described.

First, a state where the elastic members F are stretched will be described.

As shown in FIG. 2B, the first surfaces 1f and 2f of the pair of sheets 1 and 2 oppose each other or are in contact with each other. The plurality of elastic members F are arranged between the first surfaces 1f and 2f of the pair of sheets 1 and 2, and are arranged spaced apart from each other as indicated by broken lines in FIG. 2A.

As shown in FIG. 2A and FIG. 2B, the pair of sheets 1 and 2 are attached to each other by being welded (structure), without using an adhesive, at a plurality of attached portions 3. In the present example, the pair of sheets 1 and 2 are welded to the elastic members F at the attached portions 3, thereby securing the elastic members F to the pair of sheets 1 and 2 at the attached portions 3.

The attached portions 3 are formed (attached by a welded structure) as the pair of sheets 1 and 2 are welded together on the first surfaces 1f and 2f of the pair of sheets 1 and 2 of FIG. 2B. The attached portions 3 extend in the direction Dp that crosses (e.g., is perpendicular to) the direction of stretch Df of the elastic members F of FIG. 2A, and are spaced apart from each other in the direction of stretch Df.

The elastic members F may be line-shaped or chord-shaped. For example, as shown in FIG. 3(b), an elastic member F may be a multi-strand member, which is a bunch of rubber threads (elastic fibers) F1. The material of the rubber threads F1 may be polyurethane, for example.

Due to the shrinking force of the elastic members F, the stretchable sheet 10 forms a large number of folds P when the elastic members F are shrunk, as shown in FIGS. 3(a) and 3(d). The stretchable sheet 10 when the elastic members F are shrunk will now be described.

The sheets 1 and 2 may each be a thermoplastic non-woven fabric including a large number of thermoplastic fibers 11 layered together, for example.

The folds P of FIG. 3(a) are formed as the pair of sheets 1 and 2 protrude in the direction Dv as shown in FIG. 3(a) in a state where the elastic members F of FIG. 2A are shrunk.

That is, in each area a1 defined between adjacent attached portions 3 and adjacent elastic members F of FIG. 2A, non-bonded positions of the pair of sheets 1 and 2 of FIGS. 3(a) and 3(d) that oppose each other protrude in the same perpendicular direction Dv, thereby forming a fold P.

As shown in FIG. 2A, the attached portions 3 are formed in straight lines parallel to each other so that the folds P of FIG. 3(a) are formed clearly between the attached portions 3 that are parallel to each other and are formed in straight lines parallel to each other as shown in FIG. 2A.

As shown in the enlarged cross sections of FIG. 3(a), the first surfaces 1f and 2f of the pair of sheets 1 and 2 may be in contact with each other at at least some of the positions where they oppose each other to form the folds P, for example.

As shown in FIG. 3(a), at the folds P, the first surfaces 1f and 2f of the pair of sheets 1 and 2 may be in such close contact with each other that the boundary therebetween is obscure. Conversely, at the folds P, the first surfaces 1f and 2f of the pair of sheets 1 and 2 of FIG. 3(a) may be completely spaced apart from each other.

In FIG. 2A, the attached portions 3 include a plurality of strongly-attached portions 3s, a plurality of weakly-attached portions 3w and a plurality of secured portions 3f.

In FIG. 2A, strongly-attached portions 3s are hatched. Strongly-attached portions 3s are arranged on both sides of each elastic members F in the crossing direction Dp.

Weakly-attached portions 3w are dotted. Weakly-attached portions 3w are arranged between adjacent elastic members F of the elastic members F and between adjacent strongly-attached portions 3s of the strongly-attached portions 3s.

The strength of attachment between the pair of sheets 1 and 2 at the weakly-attached portions 3w is less than the strength of attachment between the pair of sheets 1 and 2 at the strongly-attached portions 3s. The strength of attachment may be measured in terms of the tension per unit area or unit length of the attached portions 3s and 3w that is required to tear the attached portions.

The difference in strength of attachment will manifest itself as the difference in thickness between the strongly-attached portions 3s and the weakly-attached portions 3w as shown in FIGS. 3(a) and 3(d), for example. That is, the thickness Tw of the weakly-attached portions 3w is greater than the thickness Ts of the strongly-attached portions 3s. This is because the welding is stronger as the sheets 1 and 2 are pressed harder against each other, and the sheets 1 and 2 melt more when being welded as the welding is stronger.

The attaching force of the secured portions 3f indicated by blanks in FIG. 2A may be weaker than or stronger than the strongly-attached portions 3s. The attaching force of the secured portions 3f may be weaker than or stronger than the weakly-attached portions 3w. This is because it is only required that the elastic members F be secured to the sheets 1 and 2.

In the secured portions 3f of FIG. 2A, the sheets 1 and 2 may be welded to the elastic members F, or some or all of the fibers of the non-woven fabric may be secured as if by tangling with the elastic members F.

When the elastic members F are secured between the pair of sheets 1 and 2 of FIG. 2B at or near the end portions of the around-torso members 91 and 91 of FIG. 1, there is no need for the secured portions 3f of FIG. 2A.

As shown in FIG. 2A, the length Lw of the weakly-attached portions 3w is greater than the length Ls of the strongly-attached portions 3s.

Next, an example of the manufacturing apparatus of the stretchable sheet 10 will be described.

Figure 4A:
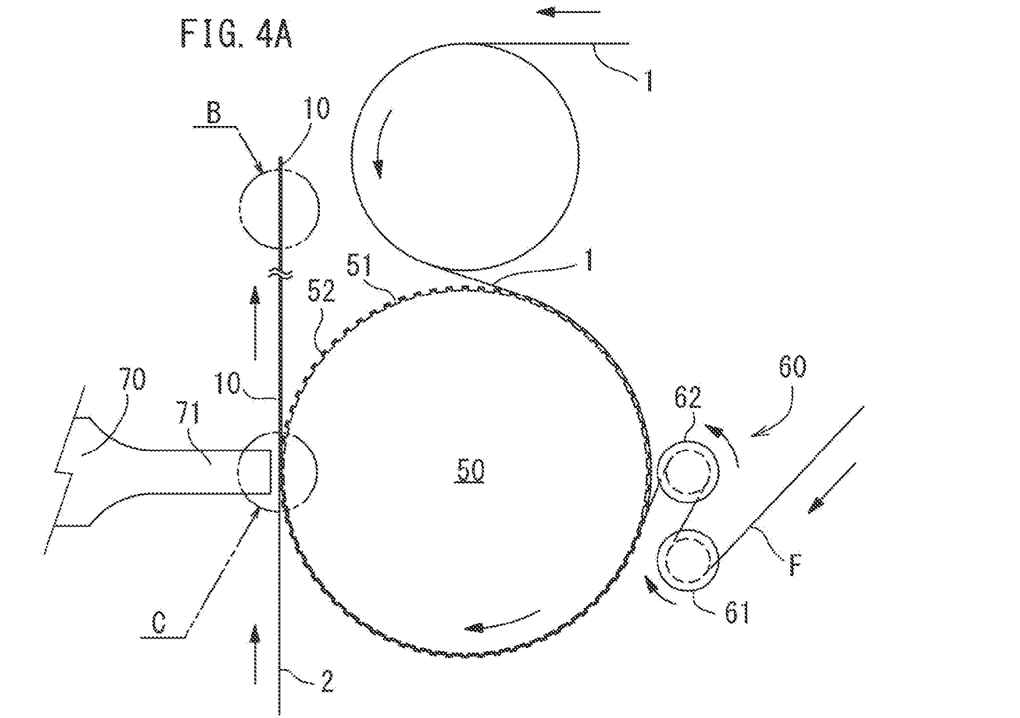
FIG. 4A is a layout diagram showing a manufacturing apparatus of the present invention.

The manufacturing apparatus of FIG. 4A includes an anvil roll 50, an introduction device 60, a welding device 70, etc.

The introduction device 60 guides and introduces the elastic members F onto the anvil roll 50. The first sheet 1 is introduced onto the anvil roll 50 at a position upstream of the position of introduction of the elastic members F, and the second sheet 2 is introduced at a position downstream of the position of introduction of the elastic members F. The anvil roll 50 carries the pair of sheets 1 and 2 and the elastic members F so that the elastic members F are arranged between the pair of sheets 1 and 2.

The welding device 70, in cooperation with the anvil roll 50, welds together the pair of sheets 1 and 2, and welds the pair of sheets 1 and 2 to the elastic members F so that the elastic members F are held by the pair of sheets 1 and 2. In the present example, the welding device 70 is an ultrasonic welding device that performs the welding with an ultrasonic energy.

The welding device 70 gives a vibration energy to a plurality of attached portions 3 of the two non-woven fabric sheets 1 and 2 of the stretchable sheet 10 of FIG. 2B, thereby welding together the two non-woven fabric sheets 1 and 2 and the elastic members F.

Figure 3:
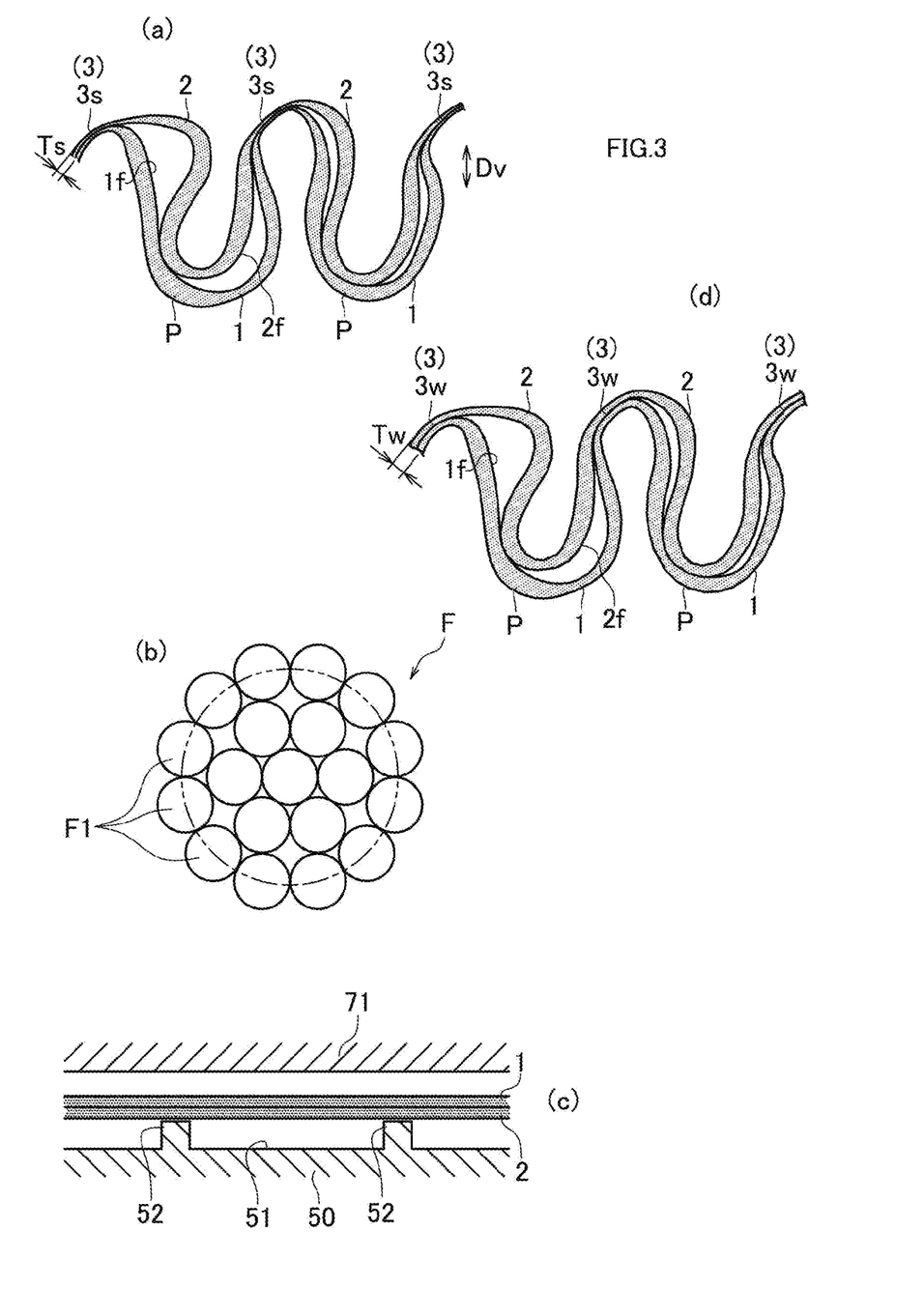
FIG. 3(a) is an enlarged cross-sectional view showing a drawing of a cross section including a strongly-attached portion of the stretchable sheet.
FIG. 3(b) is a cross-sectional view of elastic strands.
FIG. 3(c) is a cross-sectional view showing a pair of sheets in an in an unwelded state.
FIG. 3(d) is an enlarged cross-sectional view showing a drawing of a cross section including a weakly-attached portion of the stretchable sheet.
Figure 5:
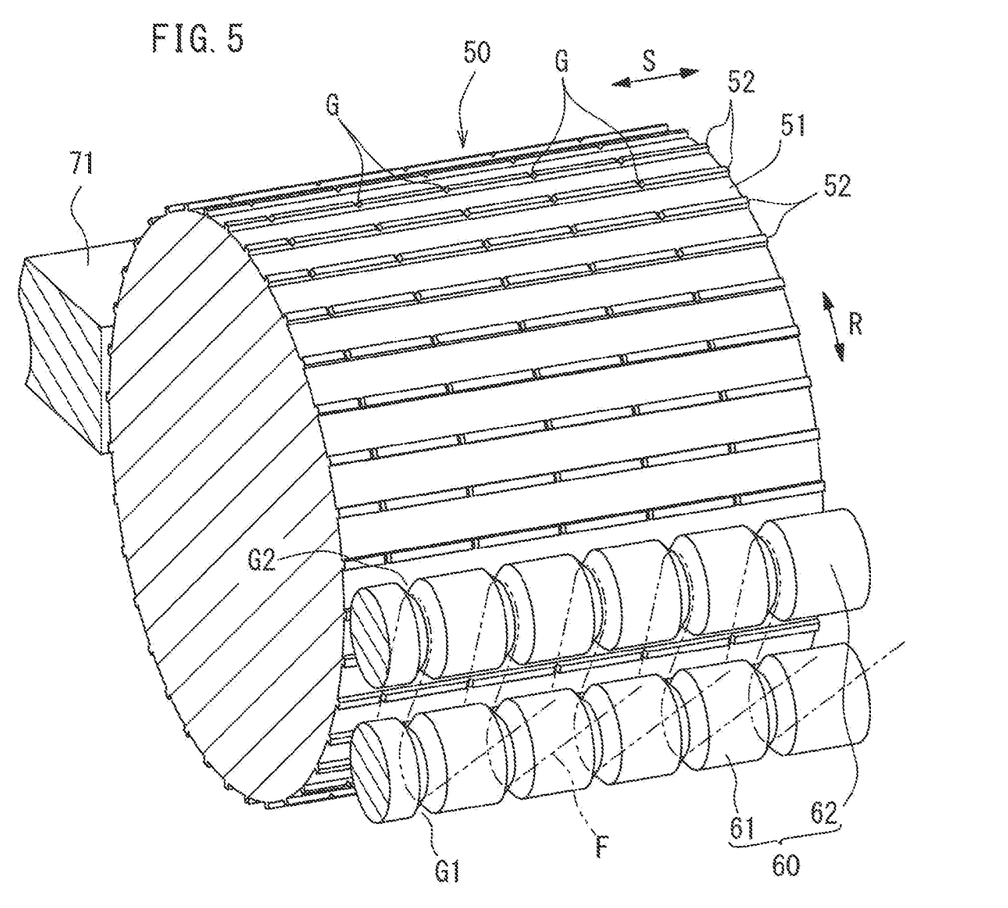
FIG. 5 is a schematic perspective view of the anvil roll as seen from the introduction device side.

More specifically, the anvil roll 50 of FIG. 5 has a large number of ridges 52, which correspond to the attached portions 3 (FIG. 3), on a circumferential surface 51. The ridges 52 extend in the width direction S of the anvil roll 50.

The welding device 70 of FIG. 4A includes the horn 71. An ultrasonic energy is given to the horn 71, and the horn 71 opposes a ridge 52 of FIG. 4C with the pair of sheets 1 and 2 and the elastic members F interposed therebetween.

Figure 4B:
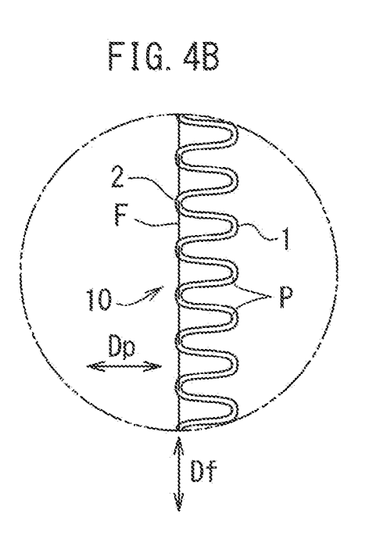
FIG. 4B is an enlarged conceptual diagram of the B part.
Figure 4C:
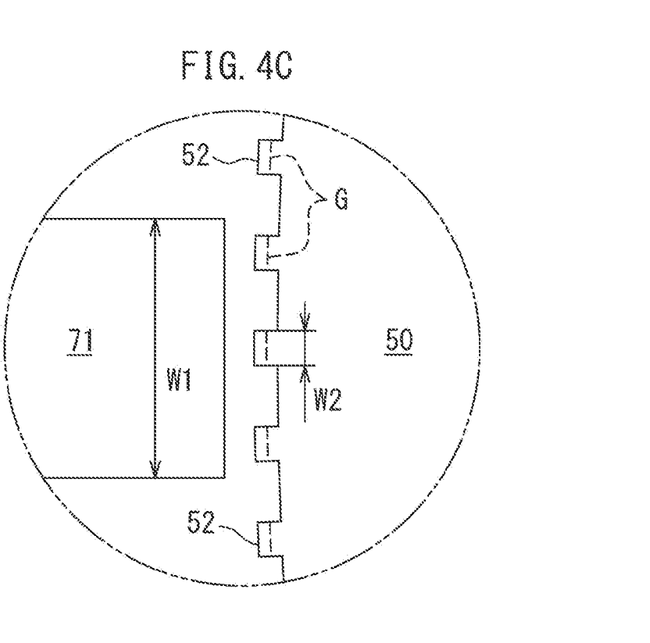
FIG. 4C is an enlarged side view of the C part.

In FIG. 4C, the width W1 of the horn 71 along the flow direction of the sheets 1 and 2 may be greater than the width W2 of the ridges 52. The setting may be such that a plurality of ridges 52 oppose the horn 71 at the same time on a temporary or non-temporary basis.

Figure 6:
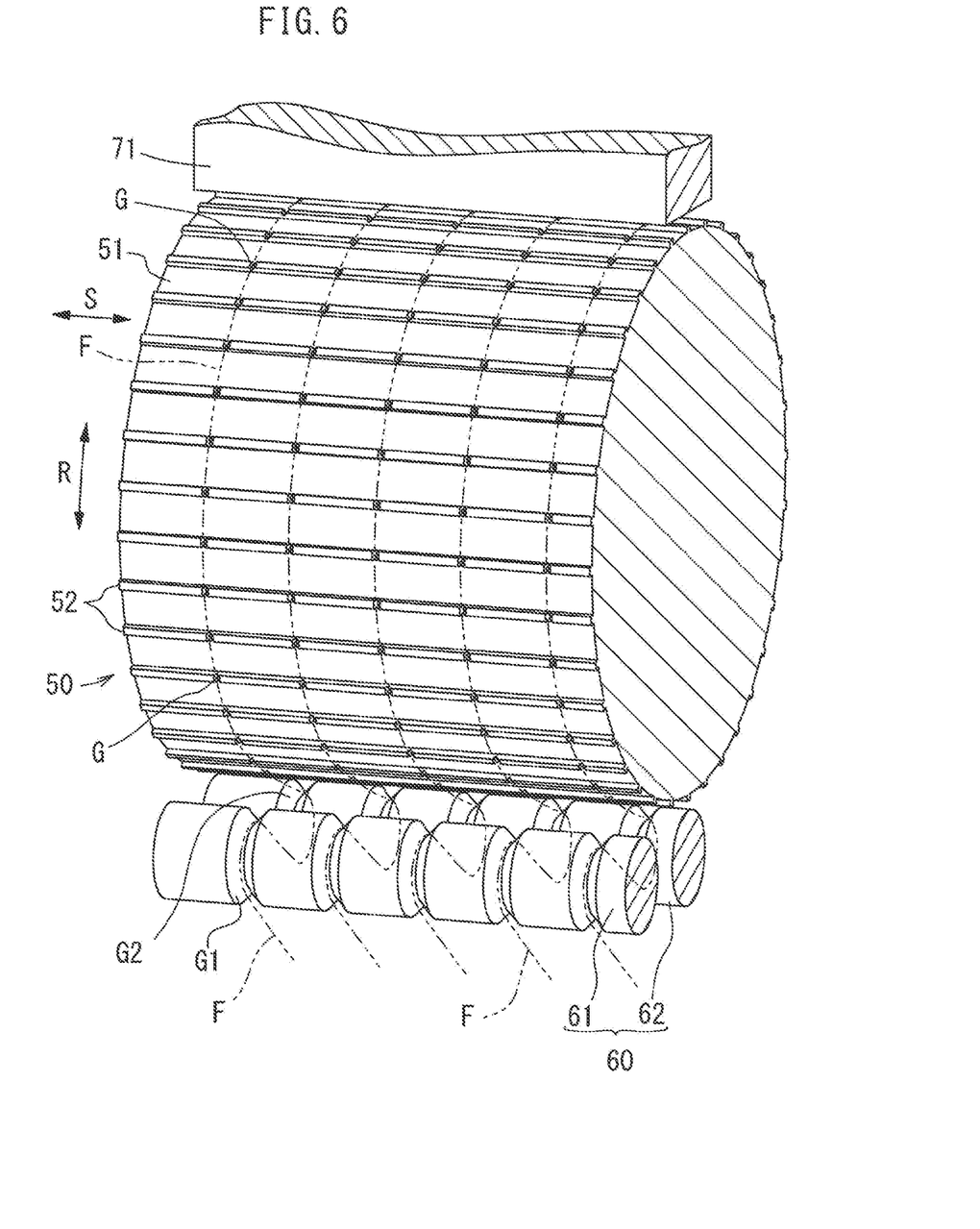
FIG. 6 is a schematic perspective view of the anvil roll as seen from below.

As shown in FIG. 5 and FIG. 6, the anvil roll 50 has a plurality of carrying grooves G. The carrying grooves G are formed in the ridges 52, extend in the circumferential direction R of the anvil roll 50 so as to cross the ridges 52, and carry the elastic members F with the elastic members F being held in the carrying grooves G. The carrying grooves G are depressed toward the center in the radial direction of the anvil roll 50.

Figure 9:
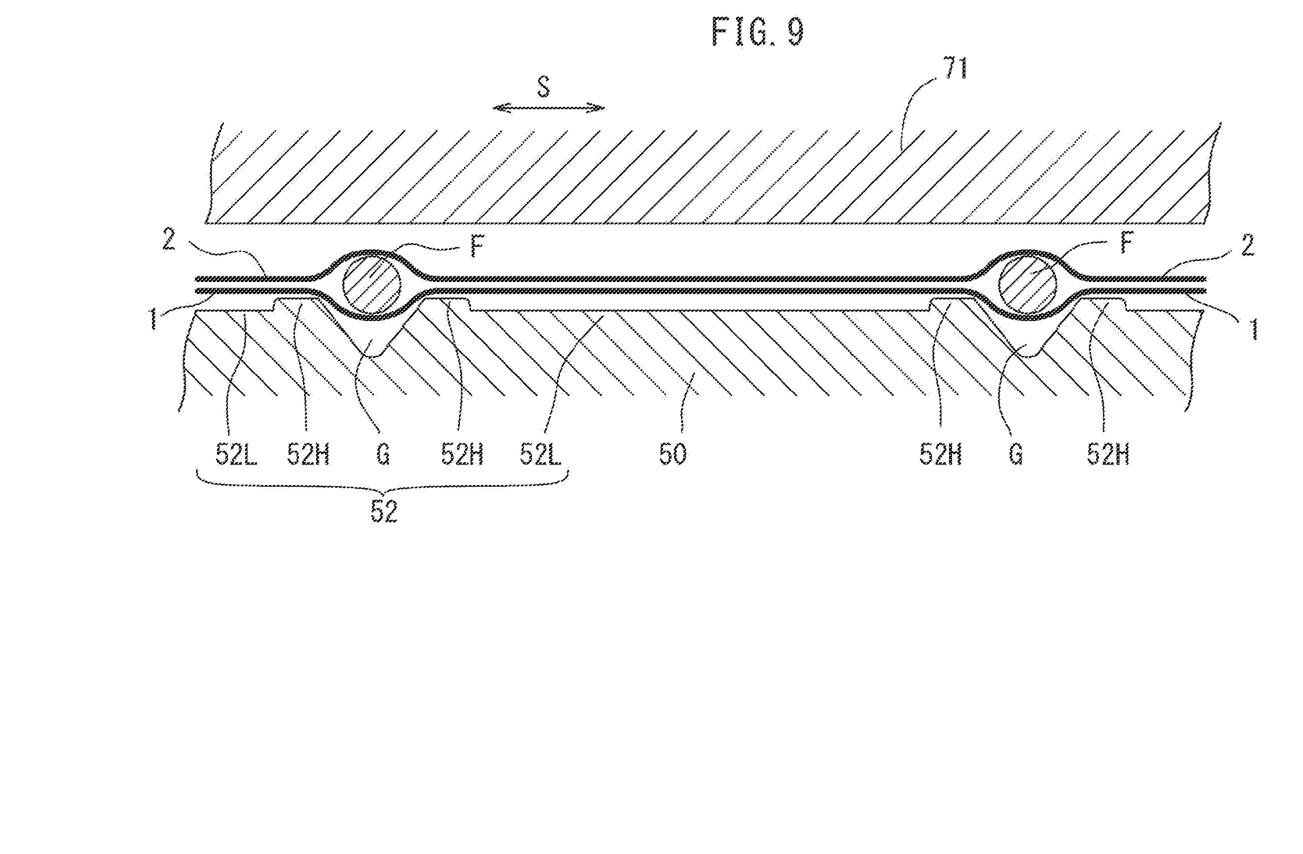
FIG. 9 is an enlarged cross-sectional view of the horn and the anvil roll taken along a ridge position of the anvil roll.

As shown in FIG. 9, the size of the carrying grooves G may be set so that the elastic members F are partly accommodated in the grooves with the remaining portion thereof lying outside the grooves. The cross-sectional area of the carrying grooves G may be smaller than the cross-sectional area of the elastic members F in natural length.

Note that although the sheets 1 and 2 are not shown in FIG. 5 to FIG. 8C, the sheets 1 and 2 are arranged so as to sandwich the elastic members F therebetween as schematically shown in FIG. 9.

The introduction device 60 of FIG. 4A includes a first roll (regulating roll) 61 and a second roll (guide roll) 62. The first and second rolls 61 and 62 of FIG. 5 may include a plurality of first and second guide grooves G1 and G2, respectively. The elastic members F are wound around the first guide grooves G1, and the first guide grooves G1 guide the elastic members F. The elastic members F, which have been guided out of the first guide grooves G1 of the first roll 61, are wound around the second guide grooves G2 of FIG. 6, and the second guide grooves G2 guide the elastic members F onto the carrying grooves G of the anvil roll 50.

The first and second rolls 61 and 62 may be free rollers, or may be rotated in sync with the anvil roll 50. The first and second rolls may be absent.

Figure 7:
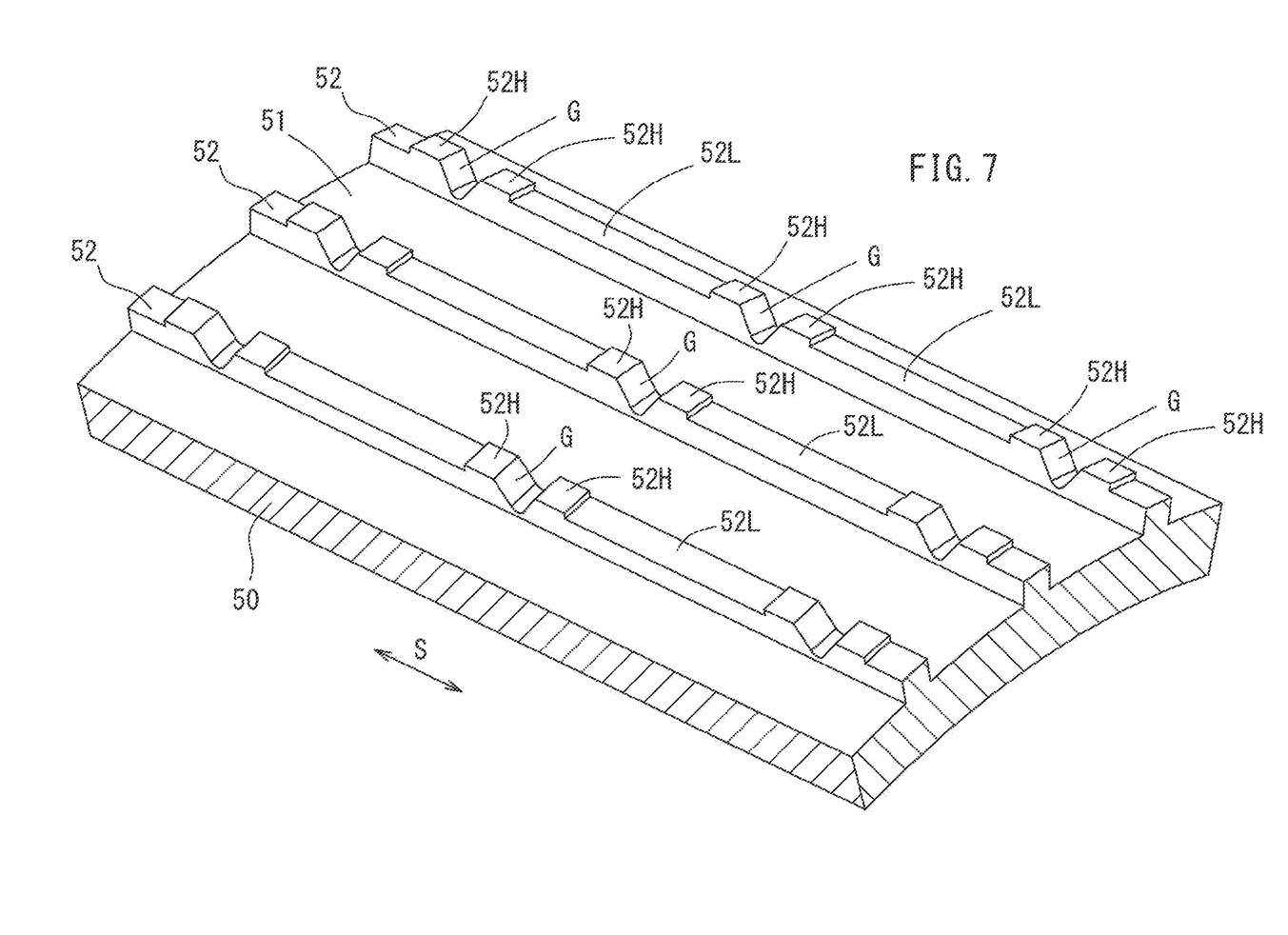
FIG. 7 is an enlarged perspective view showing a cut-out portion of the anvil roll.

As clearly shown in FIG. 7, each ridge 52 includes carrying grooves G, low ridge portions 52L and high ridge portions 52H. That is, each ridge 52 includes the high ridge portions 52H for producing the strongly-attached portions 3s, and the low ridge portions 52L for producing the weakly-attached portions 3w. Note that for ease of understanding of the structure, the heights of the ridge portions 52L and 52H and the depths of the carrying grooves G are exaggerated in FIG. 7, FIG. 8B, FIG. 8C and FIG. 9.

Figure 8A:
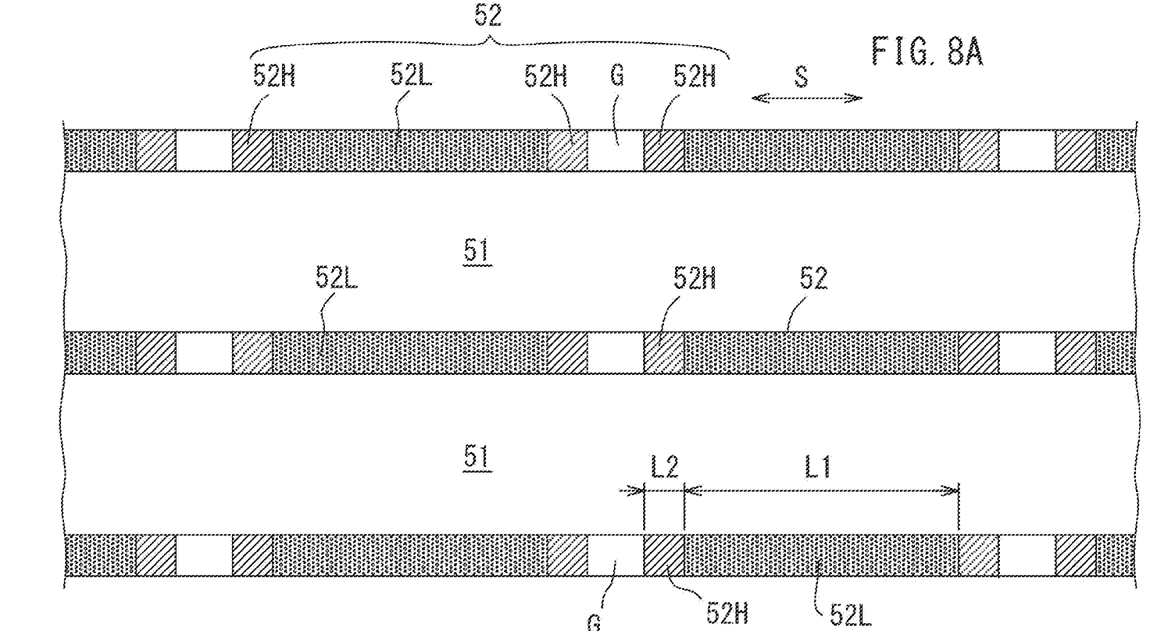
FIG. 8A, FIG. 8B and FIG. 8C are a flattened plan view, a vertical cross-sectional view and a horizontal cross-sectional view showing ridges.

In FIG. 7, the high ridge portions 52H and the low ridge portions 52L are provided intermittently in the width direction S of the anvil roll 50. In FIG. 8A, the length L1 in the width direction S of the low ridge portions 52L, which are dotted, is longer than the length L2 in the width direction S of the high ridge portions 52H, which are hatched.

Figure 8B:
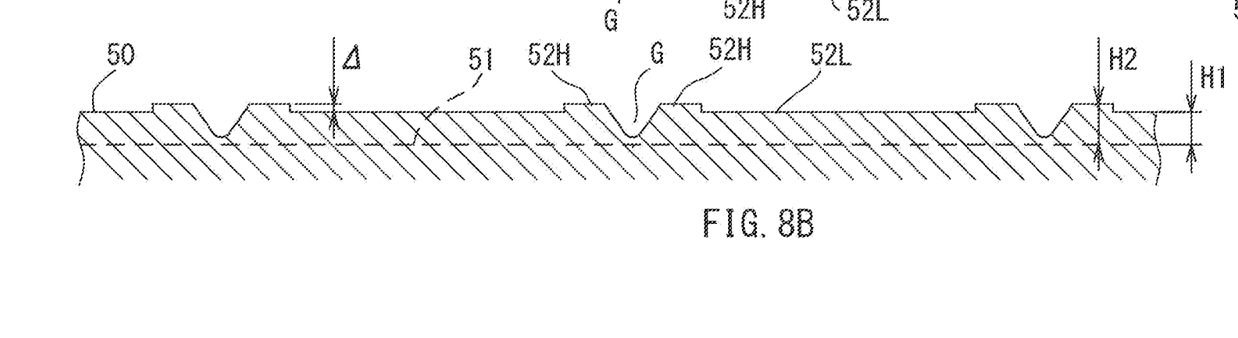
Figure 8C:
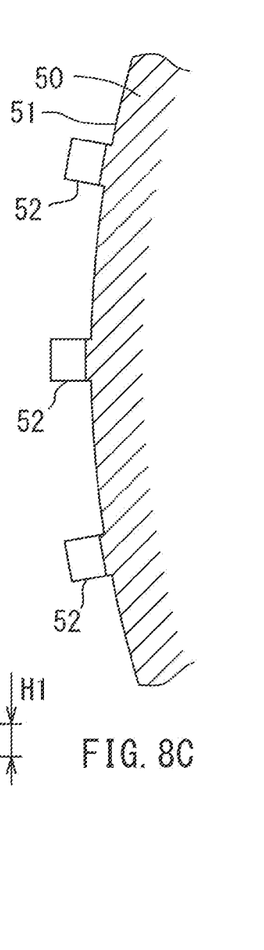

The height H1 of the low ridge portions 52L of FIG. 8B is lower than the height H2 of the high ridge portions 52H. The height H1 of the low ridge portions 52L is lower by 4 to 20 μm, for example, than the height H2 of the high ridge portions 52H.

The carrying grooves G are defined by the high ridge portions 52H that are on opposite sides in the width direction S. That is, a portion of each high ridge portion 52H is cut out in a V-letter shape, thereby forming the carrying groove G between the two high ridge portions 52H and 52H.

Next, an example of a method for manufacturing the stretchable sheet 10 will be described.

As shown in FIG. 4A, the first sheet 1 is introduced onto an upstream portion of the anvil roll 50. The elastic members F are introduced from the introduction device 60 onto the first sheet 1, which has been introduced onto the anvil roll 50. The elastic members F are carried while being held, together with the first sheet 1 (FIG. 4A), in the carrying grooves G of FIG. 4C. On the other hand, the second sheet 2 of FIG. 4A is introduced onto a position of the anvil roll 50 that opposes the horn 71.

When the first sheet 1, the elastic members F and the second sheet 2 pass through between the horn 71 and the ridge 52, the horn 71 ultrasonically vibrates toward the anvil roll 50. Thus, the sheets 1 and 2 are welded to each other, and the sheets 1 and 2 are welded to the elastic members F. Thus, the stretchable sheet 10 is produced.

Herein, as shown on an enlarged scale in FIG. 9, the pair of sheets 1 and 2 pass through between the high ridge portions 52H or the low ridge portions 52L of the ridges 52 and the horn 71 in the direction that is perpendicular to the sheet of the figure.

In FIG. 9, at the high ridge portions 52H, the horn 71 comes into contact with the second sheet 2 with a relatively large pressure. Thus, the high ridge portions 52H produce the strongly-attached portions 3s of FIG. 2A, where the pair of sheets 1 and 2 are strongly ultrasonically welded together, intermittently in the direction of stretch Df of the elastic members F.

On the other hand, in FIG. 9, at the low ridge portions 52L, the horn 71 comes into contact with the second sheet 2 with a relatively small pressure. Thus, the low ridge portions 52L produce the weakly-attached portions 3w of FIG. 2A, where the pair of sheets 1 and 2 are gently ultrasonically welded together, intermittently in the direction of stretch Df of the elastic members F.

Along the carrying grooves G of FIG. 9, the pair of sheets 1 and 2 and the elastic members F pass through between the ridges 52 and the horn 71. The elastic members F, together with the pair of sheets 1 and 2, escape into the carrying grooves G so that the horn 71 comes into contact with the second sheet 2 with a relatively small pressure. Thus, although the elastic members F are heated, it is possible to prevent the elastic members F from being excessively heated and from being melted apart.

The manufacture of the stretchable sheet 10 of FIG. 4A is performed in a flattened state where the elastic members F, the first sheet 1 and the second sheet 2 are under a tension in the carrying direction. Therefore, immediately after welding by the horn 71, the stretchable sheet 10 is produced in a flattened state as shown in FIG. 2A and FIG. 2B, and no folds appear on the stretchable sheet 10 in this state.

Then, the stretchable sheet 10 of FIG. 4A is carried downstream and is brought into a state where it is no longer under a tension in the carrying direction. In this state, folds P appear on the stretchable sheet 10 as shown in FIG. 4B.

The folds P thus produced may protrude exposed on a skin-contact surface 98 of FIG. 1, or may protrude exposed on a non-skin-contact surface opposite thereto.

Next, another example will be described with reference to FIG. 10A to FIG. 10C. Although the attached portions 3 are entirely dotted in FIG. 10A to FIG. 10C, the attached portions 3 include strongly-attached portions 3s and weakly-attached portions 3w that are not shown in the figures.

Figures 10A, 10B:
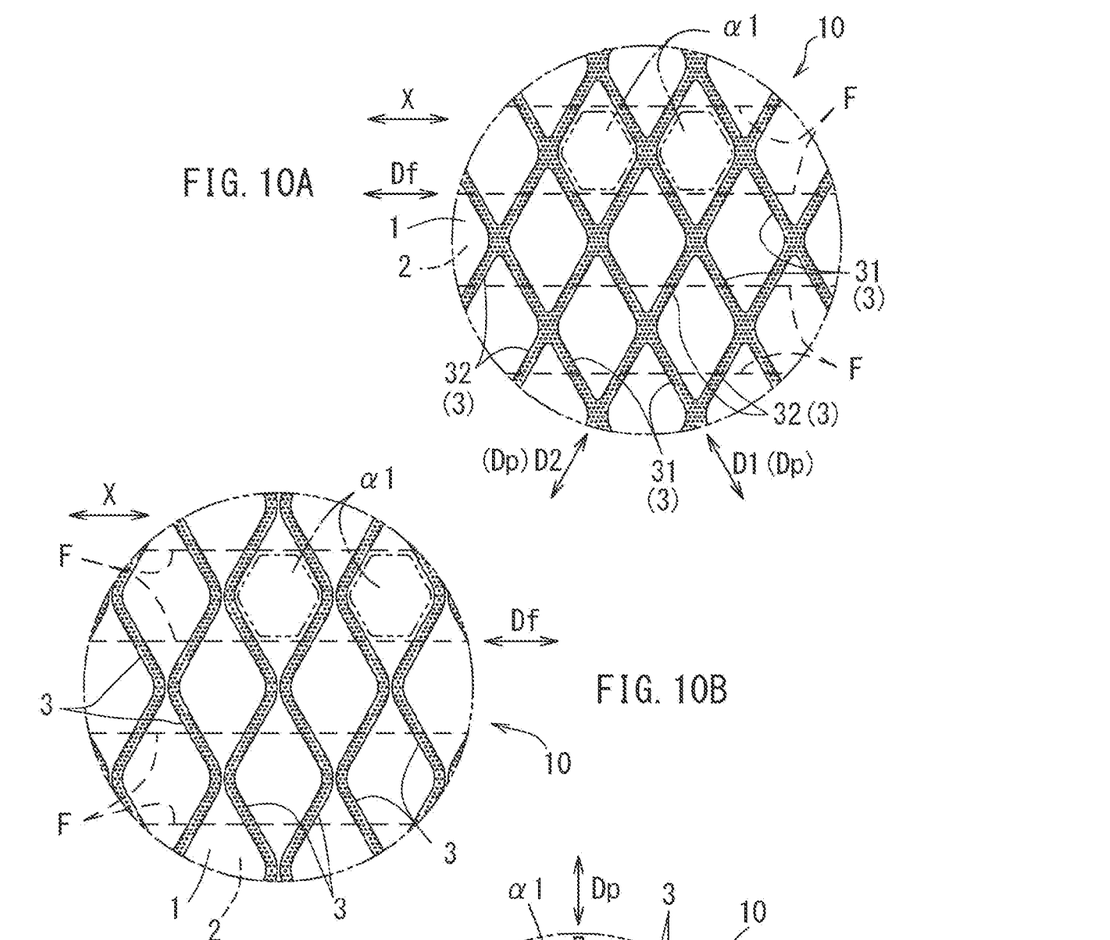
FIG. 10A, FIG. 10B and FIG. 10C are enlarged plan views showing, flattened, Embodiments 2, 3 and 4, respectively, of the stretchable sheet.

FIG. 10A shows Embodiment 2.

In the present embodiment, the attached portions 3 include a plurality of first attached portions 31 and a plurality of second attached portions 32. The first attached portions 31 extend in the first direction D1 crossing the direction of stretch Df of the elastic members F. The second attached portions 32 extend in the second direction D2 crossing the direction of stretch Df and the first direction D1.

Note that the attached portions 3 may be bent with respect to each other without crossing each other as shown in FIG. 10B.

Figure 10C:
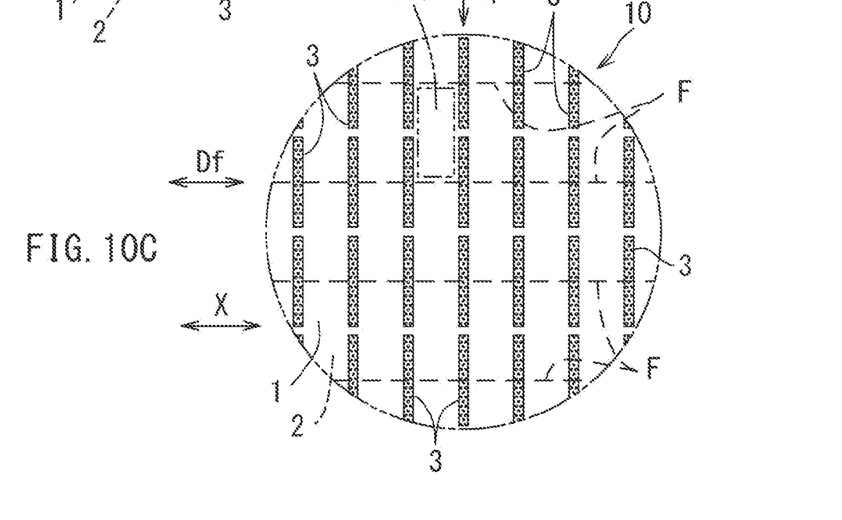

Each attached portion 3 may be non-continuous as shown in FIG. 10C.

Other structures and manufacturing methods of worn articles 1 of other embodiments are similar to those of Embodiment 1 described above, and the same portions and like portions are denoted by like reference numerals and will not be described in detail below.

While preferred embodiments have been described above with reference to the drawings, various obvious changes and modifications will readily occur to those skilled in the art upon reading the present specification.

For example, the stretchable sheet can be applied to products other than worn articles.

Embodiment 1 has been directed to a case where the length Lw of the weakly-attached portions 3w is greater than the length Ls of the strongly-attached portions 3s. Alternatively, with the stretchable sheet of the present invention, the length of the weakly-attached portions may be equal to the length of the strongly-attached portions or may be less than the length of the strongly-attached portions. In either case, the weakly-attached portions are unlikely to be broken, and it is therefore possible to prevent the attached portions from being broken continuously over a great length.

Thus, such changes and modifications are deemed to fall within the scope of the present invention, which is defined by the appended claims.

INDUSTRIAL APPLICABILITY

The present invention is applicable to a stretchable sheet that can suitably be used in diaper-type and pants-type disposable worn articles, and a manufacturing apparatus therefor.

REFERENCE SIGNS LIST 1, 2: Pair of sheets, 10: Stretchable sheet, 1f, 2f: First surface
3: Attached portion, 3s: Strongly-attached portions, 3w: Weakly-attached portions, 3f: Secured portions, 31: First attached portion
32: Second attached portion
50: Anvil roll, 51: Circumferential surface
52: Ridge, 52H: High ridge portions, 52L: Low ridge portions
60: Introduction device, 61: First roll (regulating roll), 62: Second roll (guide roll)
70: Welding device, 71: Horn
D1: First direction, D2: Second direction, Df: Direction of stretch, Dp: Crossing direction
F: Elastic member
G: Carrying groove, G1: First guide groove, G2: Second guide groove
H1, H2: Height, L1, L2: Length, Ls, Lw: Length
S: Width direction, Ts, Tw: Thickness
P: Fold, W1-W2: Width, α1: Area

The invention claimed is:

1. A stretchable sheet comprising:
a pair of sheets whose first surfaces oppose each other or are in contact with each other;
a plurality of elastic members that are arranged between the first surfaces of the pair of sheets and are arranged spaced apart from each other;
a plurality of attached portions, wherein the first surfaces of the pair of sheets are attached to each other by a welding construction without using an adhesive, at the attached portions; the attached portions hold the elastic members; the attached portions extend in a direction crossing a direction of stretch of the elastic members; and the attached portions are spaced apart from each other in the direction of stretch between adjacent elastic members of the elastic members; and
a plurality of folds that appear between the attached portions in a state where the elastic members are shrunk,
wherein the attached portions include:
a plurality of strongly-attached portions arranged on opposite sides of each of the elastic members in the crossing direction; and
a plurality of weakly-attached portions; each of the weakly-attached portions being arranged between adjacent elastic members of the elastic members and between adjacent strongly-attached portions of the strongly-attached portions,
wherein a strength of attachment between the pair of sheets at the weakly-attached portions is less than a strength of attachment between the pair of sheets at the strongly-attached portions.

2. The stretchable sheet according to claim 1, wherein a length of the weakly-attached portions is greater than a length of the strongly-attached portions.

3. The stretchable sheet according to claim 1, wherein a thickness of the weakly-attached portions is greater than a thickness of the strongly-attached portions.

4. A worn article comprising the stretchable sheet according to claim 1, wherein:
the worn article has a skin-contact surface configured to be in contact with a skin of a wearer, and a non-skin-contact surface that is opposite to the skin-contact surface; and the folds protrude on the skin-contact surface and/or the non-skin-contact surface.

5. An apparatus for manufacturing the stretchable sheet according to claim 1, the manufacturing apparatus comprising:
- an anvil roll for carrying the pair of sheets and the elastic members so that the elastic members are arranged between the pair of sheets; and
- a welding device, in cooperation with the anvil roll, for welding together the pair of sheets so that the elastic members are held by the pair of sheets, wherein:
- the anvil roll has a plurality of ridges that are formed on a circumferential surface of the anvil roll and extend in a width direction of the anvil roll;
- each of the ridges includes a plurality of high ridge portions for producing the strongly-attached portions and a plurality of low ridge portions for producing the weakly-attached portions;
- the high ridge portions and the low ridge portions are provided intermittently in the width direction; and
- a height of the low ridge portions is lower than a height of the high ridge portions.

6. The manufacturing apparatus according to claim 5, wherein a length of the low ridge portions in the width direction is longer than a length of the high ridge portions in the width direction.

7. The manufacturing apparatus according to claim 5, wherein a height of the low ridge portions is lower by 2 to 30 µm than a height of the high ridge portions.

8. The manufacturing apparatus according to claim 5, wherein:
- each of the ridges of the anvil roll includes a plurality of carrying grooves that extend in a circumferential direction of the anvil roll, and carry the elastic members with the elastic members being held in the carrying grooves; and
- each of the carrying grooves is defined by the high ridge portions that are on opposite sides of each of the carrying grooves in the width direction.

9. The manufacturing apparatus according to claim 5, wherein the welding device is an ultrasonic welding device including an ultrasonic horn that opposes the ridges with the pair of sheets and the elastic members interposed between the ultrasonic horn and the ridges, and an ultrasonic energy is given to the ultrasonic horn.

* * * * *